United States Patent [19]

Schamper et al.

[11] Patent Number: 4,720,381
[45] Date of Patent: Jan. 19, 1988

[54] ACID STABLE MONOSORBITOL ACETAL GELS

[75] Inventors: Thomas J. Schamper, Ramsey, N.J.; Martin M. Perl, Brooklyn; James D. Warren, Pearl River, both of N.Y.

[73] Assignee: American Cyanamid Company, Stamford, Conn.

[21] Appl. No.: 837,856

[22] Filed: Mar. 7, 1986

Related U.S. Application Data

[63] Continuation of Ser. No. 657,463, Oct. 3, 1984, abandoned, which is a continuation of Ser. No. 373,589, Apr. 30, 1982, abandoned.

[51] Int. Cl.$^4$ ............................ A61K 7/34; A61K 7/38
[52] U.S. Cl. ............................... 424/66; 424/DIG. 5; 424/68
[58] Field of Search ...................... 424/65, DIG. 5, 66

[56] References Cited

U.S. PATENT DOCUMENTS 4,346,079 8/1982 Roehl ............................ 424/DIG. 5

FOREIGN PATENT DOCUMENTS 0024365 3/1981 European Pat. Off. .............. 424/65
008729 1/1979 Japan ..................... 424/65
2062466 5/1981 United Kingdom ................. 424/65

Primary Examiner—Dale R. Ore
Attorney, Agent, or Firm—C. J. Fickey

[57] ABSTRACT

Clear gel antiperspirant sticks comprising (a) about 37 to 94 percent by weight of a non-reactive alkanol, (b) about 1 to 10 percent of dibenzyl monosorbitol acetal, (c) 0 to 25 percent of an emollient, (d) about 5 to 25 percent of an antiperspirant active compound, and (e) about 0 to 3 percent of a $C_{12}$ to $C_{20}$ fatty acid.

7 Claims, No Drawings

ACID STABLE MONOSORBITOL ACETAL GELS

This application is a continuation of application Ser. No. 657,463, filed Oct. 3, 1984, which is a continuation of Ser. No. 373,589, filed Apr. 30, 1982, both now abandoned.

The present invention relates to gelled antiperspirant sticks in general. More particularly, it relates to gelled antiperspirant sticks containing an acidic antiperspirant-active compound. Still more particularly, it relates to antiperspirant sticks containing an acidic antiperspirant-active compound in the presence of dibenzyl monosorbitol acetal (DBMSA) as the gelling agent, and to a method for the stabilization of said sticks against deterioration.

Many known cosmetic sticks consist largely of gelled alcoholic solutions. Sticks which exhibit a desirable transparent or translucent appearance are readily prepared using sodium stearate as the gelling agent; however, they cannot be prepared in the presence of acidic antiperspirant-active salts because the alkaline gelling agent will react with the salt. Opaque sticks are readily prepared from acidic antiperspirant salts using low melting waxy materials, such as stearyl alcohol. The sticks are stable, but there is a need for a method of making acid-stable, translucent antiperspirant sticks, particularly using dibenzyl monosorbital acetal as the gelling agent.

Dibenzyl monosorbitol acetal is a unique gelling agent, providing translucent sticks. No derivative of sorbitol or any other gelling agent has yet been found which provides sticks having equal properties. DBMSA has been known for a long time; however, it is also known that acetals are stable in alkaline or neutral media, but not in acidic media. In an acidic medium, even in the presence of small amounts of water, the acetal hydrolyzes; or, it will react with a reactive alcohol, e.g. ethanol to form a different acetal. Thus, antiperspirant sticks containing acidic antiperspirant-active compounds in the presence of dibenzyl monosorbitol acetal in reactive alcoholic solvents have not been satisfactory because, in time, especially at elevated temperatures, they deteriorate and liquidify. There is a need, therefore, to find a way to stabilize these sticks against such deterioration.

Antiperspirant sticks containing dibenzyl monosorbitol acetal and acidic antiperspirant-active salts are disclosed Roehl, U.S. Pat. No. 4,151,816 (Naarden). These sticks contain, in addition to the salt and DBMSA, a lower monohydric alcohol, such as ethanol; a di- or trihydric alcohol, such as 1,3-propylene glycol or 1,3-butylene glycol, and/or a lower polyglycol; a propylene/ethylene glycol polycondensate, having the formula:

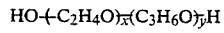

wherein $y/x+y=0.6-1$ and an average molecular weight of at least 500; and, optionally, a mono- or dialkanolamine of a higher ($C_8$–$C_{20}$) fatty acid, such as N-(2-hydroxyethyl)cocamide.

In British application No. 2,062,466 Roehl discloses that a drawback to the sticks described above is their stickiness on application, which can be eliminated by entirely omitting, or greatly reducing, the polycondensate, and adding instead about 0 to 25 percent by weight of an oleaginous compound for stickiness control.

Applicants have found that the antiperspirant sticks described by Roehl are not stable on extended exposure at an elevated temperature.

In accordance with the present invention, antiperspirant sticks are provided containing dibenzyl monosorbital acetal in the presence of acidic antiperspirant-active salts, which are stable for extended periods of time at elevated temperatures; said sticks comprising (a) about 37 to 94 percent by weight of a non-reactive solvent; (b) about 1 to 10 percent by weight of dibenzyl monosorbitol acetal; (c) 0 to 25 percent by weight of an emollient; (d) about 5 to 25 percent by weight of an antiperspirant-active compound; and (e) about 0 to 3 percent by weight of a $C_{12}$–$C_{20}$ fatty acid.

In accordance with the present invention non-reactive solvents are those which, because of the presence of less reactive alcohol groups or because of their chain length, are less reactive towards dibenzyl monosorbitol acetal in the presence of acidic antiperspirant salts; they include isopropanol, isobutanol, diethylene glycol monomethyl ether, diethylene glycol monoethyl ether, 1,3-butylene glycol, 2,3-butylene glycol, dipropylene glycol, 2,4-dihydroxy-2-pentane, N-(2-hydroxyethyl)acetamide, and the like, and mixtures thereof. Preferred compounds are 1,3-butylene glycol, 2,4-dihydroxy-2-methylpentane and N-(2-hydroxyethyl)acetamide. The amount of these nonreactive solvents used in the compositions will range from about 37 to 94 percent by weight.

A liquid volatile cyclic dimethylsiloxane may be added to the compositions to provide a dry feel and emolliency. Other commonly used emollients, such as PPG-3 myristyl ether, may also be used. Although optional, it is preferred to use from about 3 to 20 percent by weight of an emollient.

The antiperspirant-active metal compounds useful in the present invention are the usual aluminum and/or zirconium compounds, especially aluminum hydroxy chlorides. They may be used in the form of a complex to enhance solubility in alcohols, such as aluminum chlorohydroxy propylene glycol or Al/Zr chlorohydrate propylene glycol. The metal salts are preferably used in an amount of about 10 to 20 percent by weight.

When solutions of aluminum hydroxy chlorides are heated there is a tendency towards premature gelation. This may be suppressed by the addition of a small amount of a $C_{12}$ to $C_{20}$ fatty acid, such as stearic acid, without adversely affecting the stability of the gel.

In addition to the ingredients described above the antiperspirant sticks may contain a fragrance and a dye color, if desired, and other ingredients in minor amounts.

The following examples illustrate the invention.

EXAMPLE 1

The following composition was prepared in the form of a stick and was exposed to a temperature of 45° C. to determine its stability.

| Ingredient | Parts by Weight |
| --- | --- |
| N—(2-hydroxyethyl)acetamide | 80.3 |
| Dibenzyl monosorbitol acetal | 3.0 |
| Aluminum chlorohydrex | 10.0 |
| Cyclomethicone | 5.0 |
| Ethoxylated stearyl alcohol | 1.0 |
| Stearic acid | 0.5 |
| Hydroxypropyl cellulose | 0.2 |

-continued

| Ingredient | Parts by Weight |
|---|---|
| | 100.0 |

The composition was stable for more than 21 weeks at 45° C.

EXAMPLE 2

The procedure of Example 1 was followed except that 80.3 parts of 1,3-butylene glycol was used in place of 80.3 parts of N-(2-hydroxyethyl)acetamide. The resulting stick composition was stable for 18 weeks at 45° C.

EXAMPLE 3

The procedure of Example 1 was followed except that 80.3 parts of 2,4-dihydroxy-2-methylpentane was used in place of 80.3 parts of N-(2-hydroxyethyl)acetamide. The resulting stick composition was stable for 19 weeks at 45° C.

EXAMPLE 4

The procedure of Example 1 was followed except that half (40 parts) of the N-(2-hydroxyethyl)acetamide used was replaced by 2,4-dihydroxy-2-methylpentane. The resulting stick was stable for more than 21 weeks at 45° C.

EXAMPLE 5

The following stick composition was exposed at a temperature of 45° C. to determine its stability.

| Ingredient | Parts by Weight |
|---|---|
| 1,3-Butylene glycol | 53.8 |
| 2,4-Dihydroxy-2-methylpentane | 23.0 |
| Ethanol (anhydrous) | 5.0 |
| Dibenzyl monosorbitol acetal | 3.0 |
| Aluminum chlorhydrex | 15.0 |

-continued

| Ingredient | Parts by Weight |
|---|---|
| Hydroxypropyl cellulose | 0.2 |
| | 100.0 |

The composition liquified after 10 weeks at 45° C.

The example illustrates that as little as 5% ethanol, in admixture with 75.8% of less reactive solvents, causes the stick to be unstable.

We claim:

1. A solid, transparent, gelled antiperspirant composition consisting essentially of:
   (a) about 1 to 10 percent by weight of dibenzyl monosorbitol acetal as a gelling agent;
   (b) 37 to 94 percent by weight of a solvent non-reactive with said dibenzyl monosorbitol acetal which is selected from the group consisting of $C_3$ to $C_6$ aliphatic secondary alcohol, $C_4$ to $C_6$ aliphatic dihydric alcohol and mixtures thereof;
   (c) 0 to 25 percent by weight of an emollient;
   (d) about 5 to 25 percent by weight of an antiperspirant-active metal salt; and
   (e) about 0 to 3 percent by weight of a $C_{12}$ to $C_{20}$ fatty acid.

2. A composition according to claim 1 wherein (b) is selected from 1,3-butylene glycol and 2,4-dihydroxy-2-methylpentane, N-(2-hydroxyethyl)acetamide and mixtures thereof.

3. A composition according to claim 1 wherein the acidic antiperspirant-active metal salt is aluminum chlorohydrex.

4. A composition according to claim 1 wherein the acidic antiperspirant-active metal salt is aluminum chlorhydroxy propylene glycol.

5. A composition according to claim 1 wherein the acidic antiperspirant-active metal salt is aluminum-zirconium.

6. A composition according to claim 1 wherein the amount of said emollient is from about 3 to 20 percent by weight.

7. A composition according to claim 6 wherein said emollient is a cyclic dimethylsiloxane.

* * * * *